United States Patent [19]

Mack et al.

[11] Patent Number: 4,931,256
[45] Date of Patent: * Jun. 5, 1990

[54] APPARATUS FOR DILUTION AND MEASUREMENT IN AUTOMATED IMMUNOASSAY TECHNIQUES

[75] Inventors: Daniel R. Mack, Half Moon Bay; Alfred H. Sturtevant, Palo Alto; Henry L. Schwartz, Los Gatos, all of Calif.

[73] Assignee: Sequoia-Turner Corporation, Mountain View, Calif.

[*] Notice: The portion of the term of this patent subsequent to Feb. 7, 2006 has been disclaimed.

[21] Appl. No.: 217,829

[22] Filed: Oct. 11, 1988

Related U.S. Application Data

[63] Continuation of Ser. No. 888,810, Jul. 22, 1986, abandoned, which is a continuation-in-part of Ser. No. 757,785, Jul. 22, 1985, abandoned.

[51] Int. Cl.⁵ .............. G01N 35/04; G01N 35/06
[52] U.S. Cl. .................... 422/65; 422/67; 422/73; 436/809
[58] Field of Search .............. 422/63.67, 73, 100, 422/102, 104; 436/47, 49, 809

[56] References Cited

U.S. PATENT DOCUMENTS 4,803,050  2/1989  Mack ............................ 422/65

Primary Examiner—Michael S. Marcus
Attorney, Agent, or Firm—Limbach, Limbach & Sutton

[57] ABSTRACT

Apparatus are provided which automatically add diluent/quench reagent in such a manner as to enable adequate mixing as well as a short period for further mixing in automated immunoassay techniques. The probes for adding the diluent/quench reagents are offset from the optics module probe so that reagents are being added to a second row while the optics probe aspirates solutions from a first row.

5 Claims, 6 Drawing Sheets

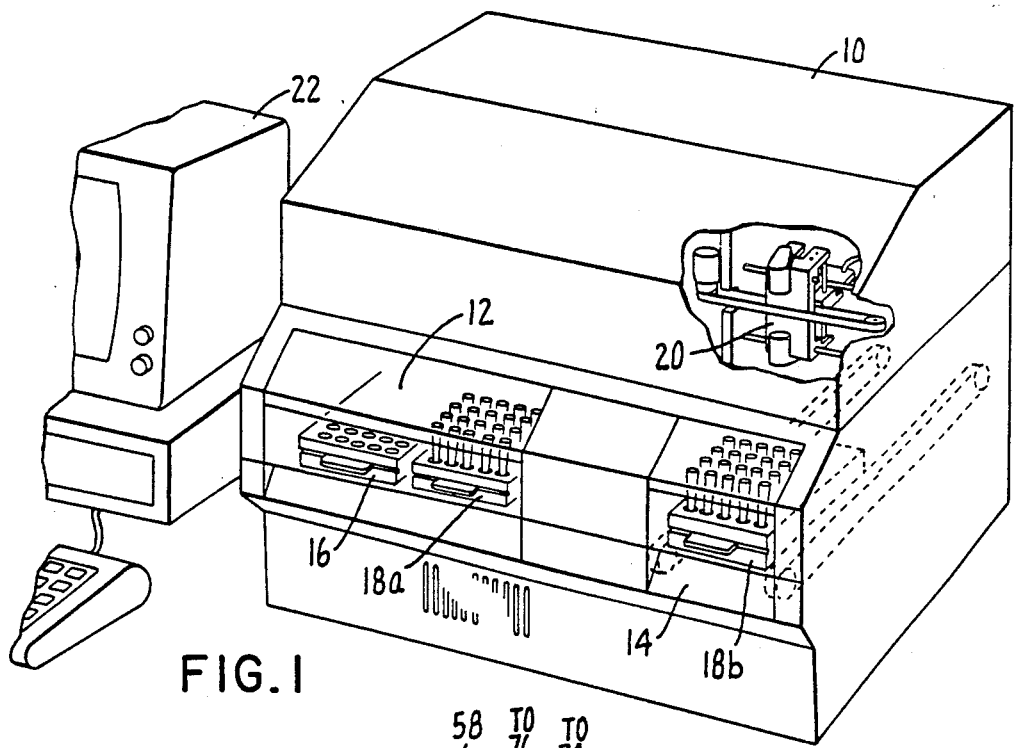
FIG.1
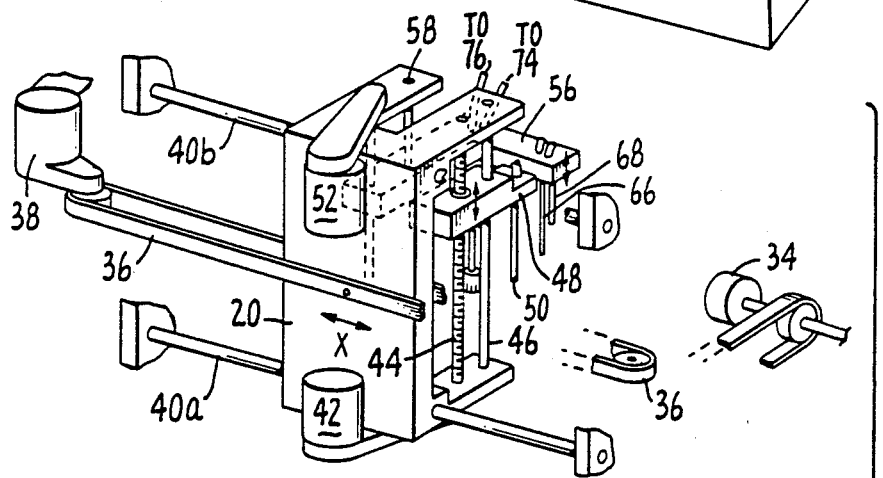
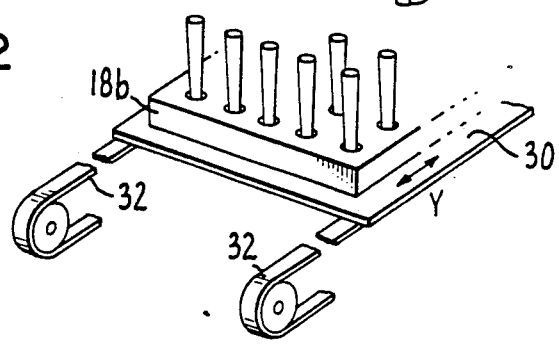
FIG.2

APPARATUS FOR DILUTION AND MEASUREMENT IN AUTOMATED IMMUNOASSAY TECHNIQUES

This application is a continuation of application Ser. No. 06/888,810, filed on July 22, 1986, now abandoned, which application was a continuation in part of application Ser. No. 757,785, filed on July 22, 1985, now abandoned.

TECHNICAL FIELD

This invention relates generally to automated instruments for performing bioassay techniques, and more specifically, to method and apparatus used to accomplish adequate mixing within reaction tubes of an immunoassay analyzer.

BACKGROUND OF THE INVENTION

The automation of immunoassay techniques which have well defined specifications has spawned a series of improvements making the automation of such processes possible. A series of applications assigned to a common assignee covering these devices and methods have been filed July 22, 1985 under the titles METHOD AND APPARATUS FOR PERFORMING AUTOMATED, MULTI-SEQUENTIAL IMMUNOASSAYS U.S. Pat. No. 4,816,418, TUBE TRAP APPARATUS, U.S. Pat. No. 4,713,218, PROBE WASH STATION U.S. Pat. No. 4,730,631, and, METHOD AND APPARATUS FOR REMOVING UNBOUND COMPONENTS IN AUTOMATED IMMUNOASSAY TECHNIQUES U.S. Pat. No. 4,803,050, and PULSE EDITING APPARATUS AND METHOD now abandoned. The relevant portions of these applications are hereby incorporated by reference into this application.

The problem to which this particular invention is addressed concerns the addition of a diluent and/or a quenching reagent to a reaction solution before the solution is measured in an optical reader to obtain absorbance or fluorescence measurements. To be able to run several racks of assays sequentially, no one rack must occupy the instrument for too long a period. Accommodating the necessary mixing and reaction times inherent to the immunoassay techniques proves difficult in view of cycle time limitations. In the steps of the technique following incubation of the sample, solid support and conjugate, the solid support is washed to remove traces of unbound antibody and conjugate reagents and a substrate reagent is added. Subsequently, after another incubation period a diluent and/or a quenching reagent are added to the reaction tube to obtain an optically detectable substance. The addition of these liquids to the washed solid support must be made in such a way that the solution is uniformly mixed to insure the accuracy and precision of the optical determination. When the addition of the diluent/quench is accomplished manually, the sample can be vigorously agitated and provided with extra time to accomplish uniform mixing. In the automated procedure, neither of these aspects of manual mixing were easily accommodated into the short cycle time made necessary by the automation of this procedure.

The subject invention provides for adding the diluent and/or quenching reagent to one row of reaction tubes through a reagent probe and offsetting by one row from the reagent probe the optic probe that simultaneously aspirates previously diluted quenched sample into the optical reading system. The simultaneous addition of the diluent/quench and the aspiration/optical reading can be accomplished in less than 17 seconds per sample so the addition of diluent/quench for a given row of five samples can be accomplished in 85 seconds. The offset of the diluent/quench and reading in successive rows provides 85 seconds for good mixing to occur between the addition of the diluent/quench reagents and the reading of the result. Furthermore, the probe dimensions are selected so that the diluent is added from a height above the eventual surface of the liquid in the reaction tube in a forceful manner to facilitate mixing. The movement of the rack in which the reaction tubes are stored also helps the mixing process.

It is therefore an object of this invention to provide reagent and optics module probes which are located on the same carriage.

It is a further object of this invention to provide sufficient mixing in an automated instrument for immunoassay techniques to provide a uniform solution for optical reading.

It is still a further object of this invention to provide for sufficient mixing to occur between the addition of the diluent/quench and the reading of the result in a short period of time, enabling the rapid throughput which is required for clinical applications of automated techniques.

SUMMARY OF THE INVENTION

The instant invention provides for an apparatus which comprises a carriage, a first probe assembly attached to that carriage, a reagent probe subtended from the first probe assembly, a second probe assembly also attached to the carriage, an optics module probe subtended from the second probe assembly, platform means for selectively positioning a rack of tubes relative to the carriage and means for simultaneously operating the diluent/quench probe of the first probe assembly and the optics module of the second probe assembly on tubes in different rows of the rack.

DESCRIPTION OF THE DRAWING

FIG. 1 is a perspective view of apparatus for performing automated, multi-sequential immunoassays and incorporating the present invention.

FIG. 2 is an enlarged exploded perspective view of a portion of the structure shown in FIG. 1.

DETAILED DESCRIPTION OF THE INVENTION

Figure 3:
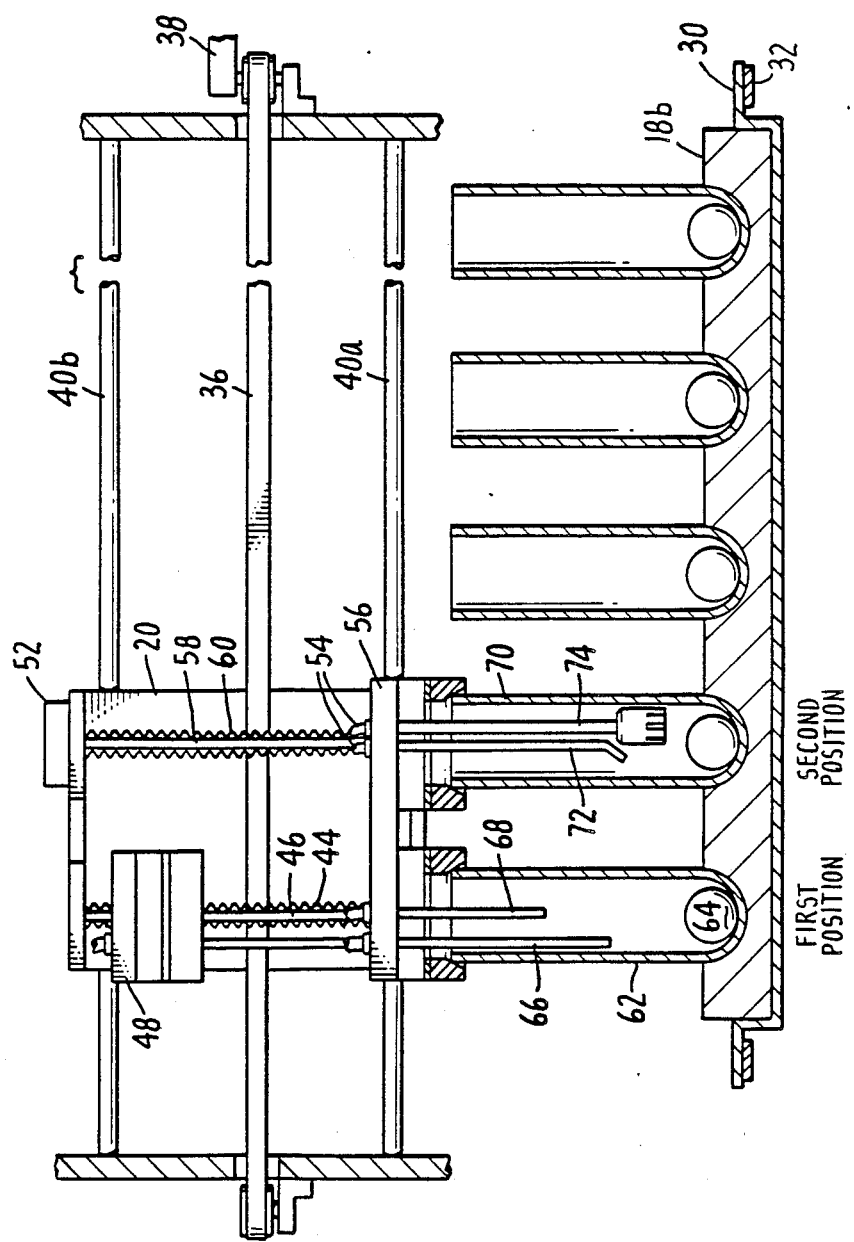
FIG. 3 is an enlarged elevational sectional view of a portion of the structure shown in FIG. 2.

While the subject invention is described with reference to a particularly preferred embodiment, here the Hybritech Immunochemistry Analyzer, it is to be appreciated by those skilled in the art that other embodiments are possible which are encompassed within the scope of the present invention and are intended to be within the scope of the claims appended hereto.

The immunochemistry analyzer 10 is shown in FIG. 1. The analyzer has a sample processing module 12 and a reaction processor module 14. Sample cups held in rack 16 are loaded into the sample module 12 where the serum is transferred from cups in rack 16 to reaction tubes held in rack 18a. In the preferred embodiment each of the reaction tubes contains a solid sphere to which is bound one member of the immunological pair used in the "sandwich" technique. As described above, after the diluted serum is placed in the reaction tubes, and conjugate reagent is added to the tubes, the entire rack 18a is removed from the instrument and undergoes a carefully timed incubation period, the length of which is determined by the particular assay being performed.

At the end of the antigen-antibody incubation period, the operator returns the rack 18b containing reaction tubes to the reaction processor module 14. As seen through the partially broken away front face of the unit, carriage 20 is positioned above the rack 18b to effect horizontal and vertical movement of the probes relative to the rack 18b and tubes. In this preferred embodiment, a personal computer 22, e.g. an IBM PC-XT, is used to control the movement of the carriage 20 and to time the various steps of the assay protocol, both on and off of the instrument 10.

The reaction processor module of the preferred embodiment is detailed in FIG. 2. The reaction tube rack 18b consists of a rectangular array of rows and columns of holes for receiving reaction tubes. Carriage 20 moves across the rows and has no component of movement in the "column" vector. However, those skilled in the art will recognize that the carriage 20 may easily be designed to effect y-direction movement. Movement of the rack 18b relative to the carriage 20 is accomplished by a table or platform 30 underneath the rack 18b. The table 30 is motor-driven in the direction of the "column" vector. The movement of this platform is controlled by table drive belts 32, table motor 34 and an automatic controller which in this preferred embodiment comprises an IBM personal computer. The controller controls the table 30 movement in discrete units equivalent to the distance between rows. The controller also controls the lateral movement of the carriage 20 in discrete movements equivalent to the width of one column. Thus, between the movement of the carriage 20 and the table 30, the probe assembly which is attached to the carriage 20 can be positioned over every tube contained within the rectangular matrix.

The carriage 20 is conveyed in the x-direction by carriage drive belt 36, driven by a carriage motor 38. Guide rods 40a and 40b ensure accurate movement of the carriage in the x-direction to permit proper registration of the probes with the tube mouth.

Affixed to carriage 20, there are two probe assemblies 48 and 56 operating independently in the vertical direction. The first probe assembly 48 carries a read or optics probe 50 which aspirates fluid from the tubes into an optics module for quantitative optical determination. The second assembly 56 carries adjacent detergent add and aspirate probes 72 and 74, respectively, utilized in the wash cycle, and a substrate probe to add substrate reagent for chromophore formation. Also, the second assembly 56 carries a diluent/quench probe 68 adjacent the substrate probe 66 but for the read cycle. The optics probe 50 is spaced from probes 66 and 68 by the distance between rack rows.

Vertical movement of the first probe assembly 50 is accomplished by a first probe motor 42 which drives jack screw 44. A guide rod 46 fixes the position of a first probe assembly 48 in the horizontal plane, to permit registration of the probe 50 with the reaction tubes. Second probe motor 52 controls vertical movement of probes 72 and 74 which are depended from the second probe assembly 56. The probe motor 52 drives a jack screw (shown in dashed lines) fixed to the bottom of the carriage 20. Guide 58 fixes the horizontal position of the second probe assembly 56. The direction of the jack screw drive determines whether the probe assembly ascends or descends. Probe 72 adds detergent solution to, and probe 74 aspirates the same from, the tubes.

Referring now to FIG. 3, second probe assembly 56 and its associated mechanisms can be seen here clearly. Guide 58 and jack screw 60 are shown in relation to the second probe motor 52 which drives jack screw 60.

FIG. 3 shows reaction tube 62 in which a spherical support 64 is placed according to the immunoassay protocol. In tube 62 are substrate probe 66 and diluent/quench probe 68 and in a tube 70, identified as being in the "second" position in rack 18b, are detergent dispensing probe 72 and aspirating probe 74, all depending from the second probe assembly 56. It is also shown in FIG. 3 that the probes and their respective assemblies can be withdrawn from the tubes to permit movement of either the carriage 20 or the rack 18b, or both.

Figure 4:
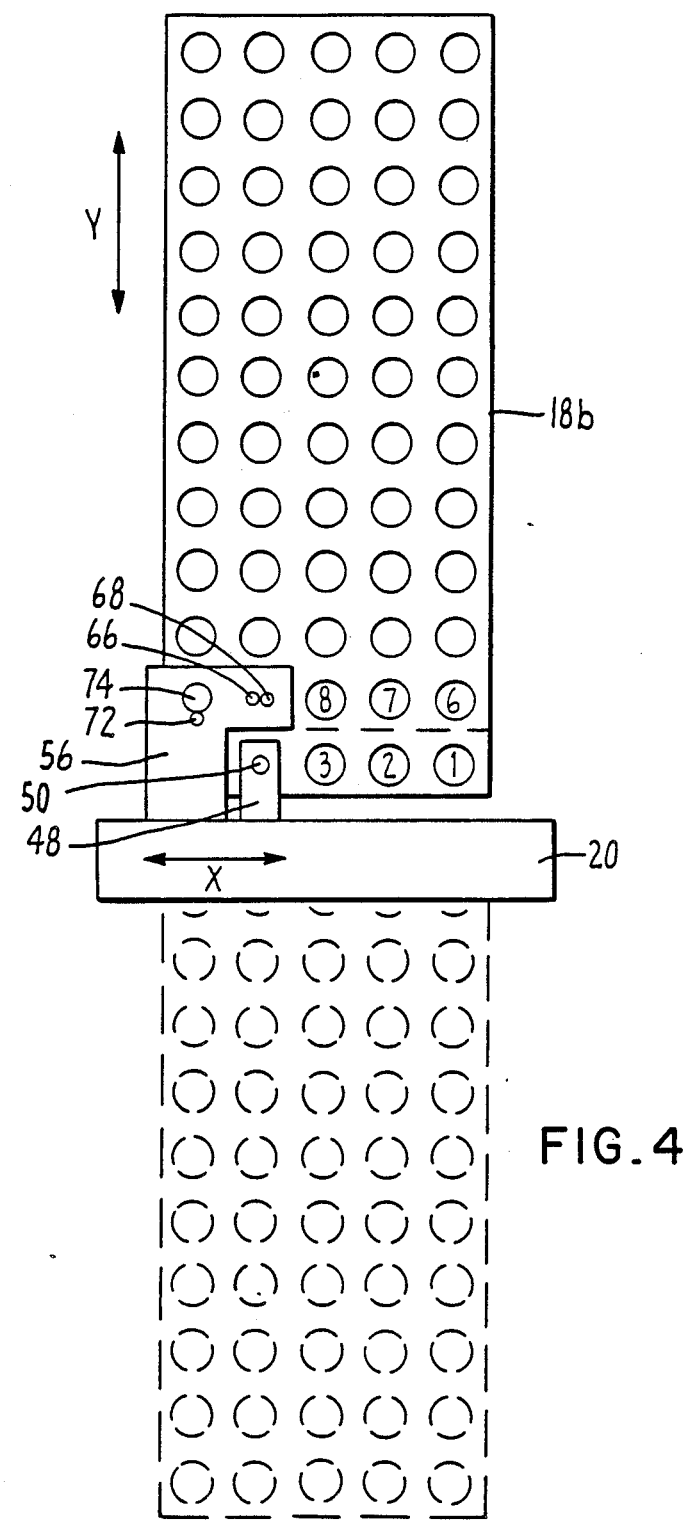
FIG. 4 is a top schematic view of the reaction processor module of the instant invention for illustrating the wash cycle.

Referring to the top plan view of FIG. 4, the relationship between the rack 18b, carriage 20 and the probe assemblies 48 and 56 is shown. Carriage 20 causes movement in the x-direction, along the rows of the rack 18b. Table 30, underneath rack 18b causes the rack 18b to be moved in the y-direction, along the columns of the rack. While this embodiment is described with reference to a carriage having x-direction movement and a table accomplishing y-direction movement, two carriages can be used, or the table can effect x-direction movement. Each of these various configurations is intended to be within the scope of this invention.

Referring to FIG. 4, the wash cycle according to the present invention will be described. Row 1, consists of five positions 1 through 5, and row 2, consists of positions 6 through 10. Positions 4, 5, 9 and 10 are covered by the probe assembly 56. This wash cycle commences after the antibody-antigen incubation period which occurs off the machine has ended and the rack 18b has been loaded into the reaction processor module. Once the automatic controller has confirmed the identity of the rack 18b and the type of assay to be performed, the wash cycle begins when the wash probe is inserted into the first tube in the first row (position 1).

For each individual tube, the first part of the wash cycle consists of aspirating the reagents and sample serum from the tube through probe 74, adding detergent through probe 72 and aspirating detergent through probe 74. These aspiration and addition steps are repeated again with the final step in the first half of the wash cycle being to add detergent to the tube through probe 72. The probe assembly 56 then extracts the wash probes 72 and 74 from the first tube. Commencing with the tube in position 1, the above described series of detergent addition-aspiration steps occur, leaving tube 1 with a volume of detergent in which to soak. The wash probes 72 and 74 are then removed from the tube in the first position.

After detergent has been added to each of the tubes in positions 1 through 5, and the probes 72 and 74 have moved through the sixth position, the rack table is activated to move the rack one row's distance forward relative to the probes 72 and 74. Thus, the probes 72 and 74 are registered with a tube in position 6. The probes 72 and 74 then go through the first half of the wash cycle in position 6. After the probes 72 and 74 are removed from the tube in position, 6, the rack table is activated to move the rack one row's distance rearward relative to the probes 72 and 74. This time the movement of the rack is in the reverse, positioning probes 72 and 74 above the tube in position one. This tube one has been soaking in the detergent dispensed in the first pass through row one. However, in this half of the wash cycle, the detergent previously dispensed is aspirated through probe 74 and one final aliquot of detergent is dispensed through probe 72. The final step in the wash cycle is to vacuum dry the tube in position one by aspirating through probe 74. Thereafter, the rack table is again activated and the probes 72 and 74 are positioned over tube 7 for the first half of the wash cycle. When the rack again shifts to permit the second half of the wash cycle in tube 2, the substrate probe 66, offset by one column, is inserted into tube 1 and substrate reagent is added to the dry tube one.

The complete wash cycle takes about 19 minutes and the rack 18b is shifted to the back of the machine for a programmed 11 minute incubation period (the first tube has already incubated almost 19 minutes. Then the rack 18b is repositioned with the first row under the carriage.

Figure 5:
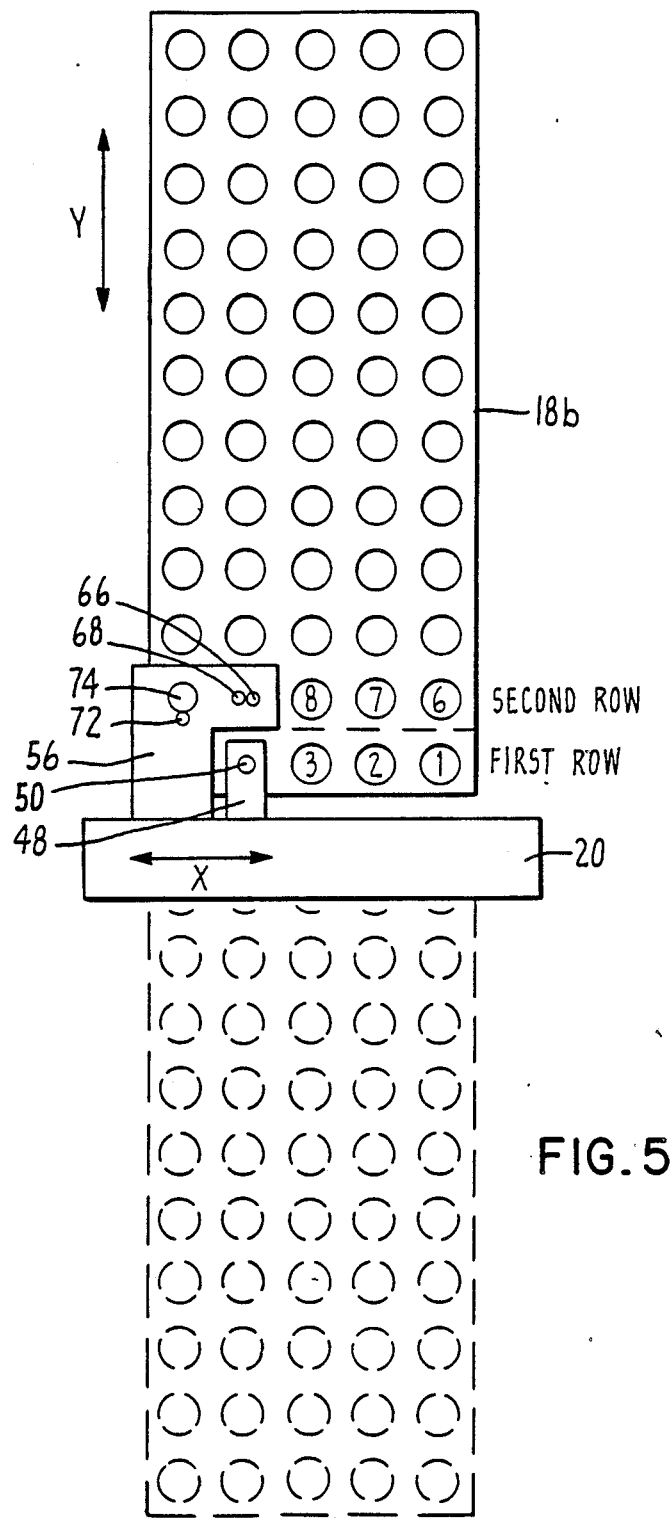
FIG. 5 is a top schematic view of the reaction processor module of the present invention illustrating the read cycle.

The method of this invention is more clearly set forth with reference to FIG. 5. Beginning in the first row, the diluent/quench probe 68 injects fluids into each of the reaction tubes in the first row, moving from right to left. After the addition of these fluids is completed, the platform is activated by the automatic controller and displaces the rack 18b of tubes by one row. FIG. 5 shows the probes 66 and 68 positioned over the fourth tube in the second row of sample tubes. As will become more apparent from the description below, diluent/quench has already been added to the tubes of the first row and the first three tubes of the second row. The solution in the first three tubes of the first row has been read or analyzed.

When the diluent/quench probe 68 is positioned over the first tube in the second row, the optical probe 50 is positioned over the first tube in the first row. The probes of this first probe assembly 48 are lowered into the tubes of the appropriate tube therebelow. As the diluent/quench probe 68 fills a reaction tube with diluent and/or quench reagents, the optics module probe 50 aspirates the solution from the correspondingly numbered reaction tube in the preceding row into a flow cell within the optics module. Depending upon the assay protocol selected previously, the optics module will obtain spectrophotometric or spectrofluorometric readings.

Figure 6:
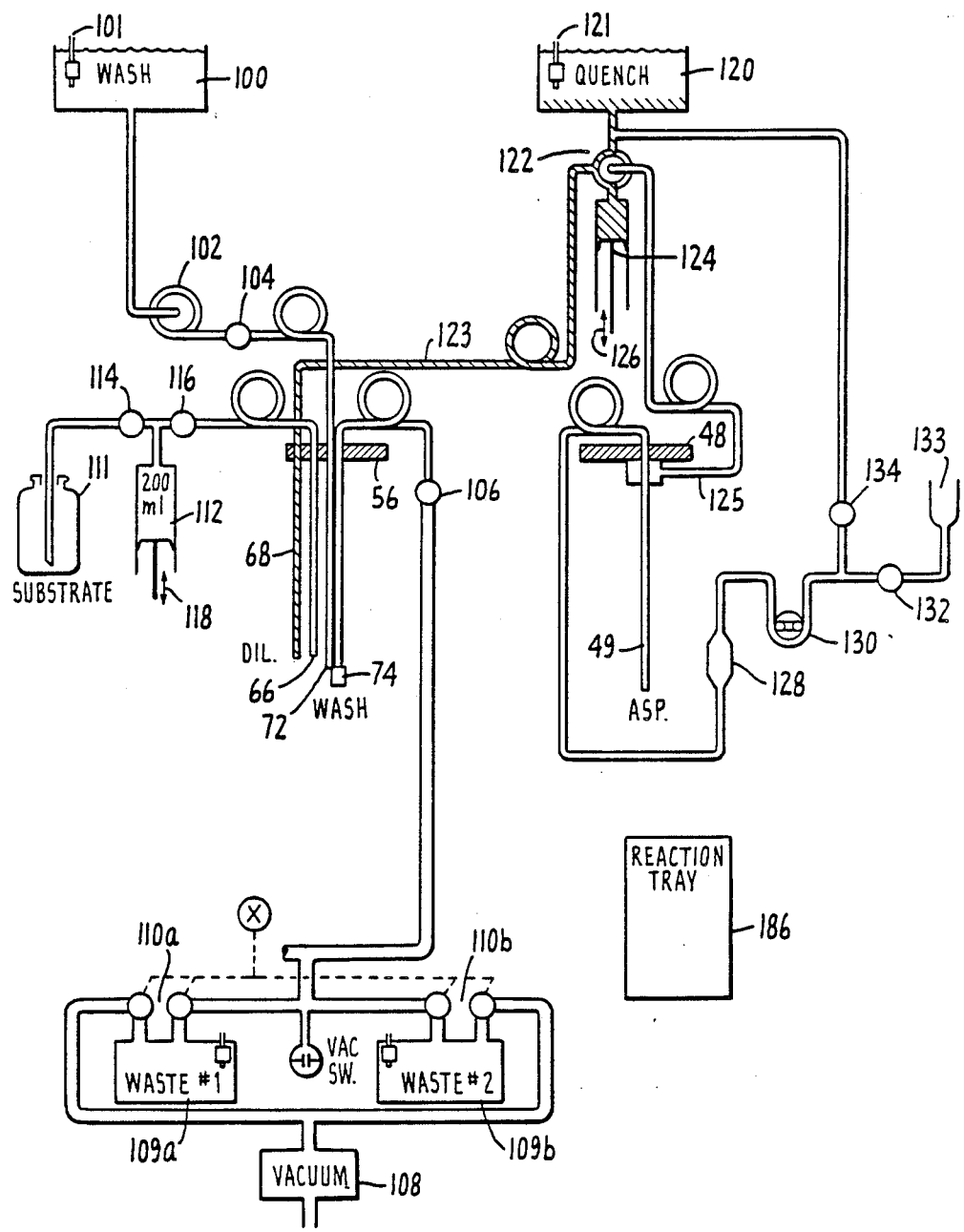
FIG. 6 is a schematic flow diagram.

FIG. 6 shows how the various fluids are delivered and aspirated on the reaction processing module. In the upper left of the figure, wash fluid is stored in a wash reservoir 100 whose liquid level is sensed by a wash liquid level sensor 101. Wash fluid flows from wash reservoir 100 to probe wash pump 102. A wash line solenoid 104 is used to open and close the valve in the wash fluid line. Wash fluid, also referred to in the specification as detergent, is dispensed from the detergent probe 72, depended from second probe assembly 56. In this embodiment, detergent is forcefully ejected from probe 72 to ensure sufficient agitation and mixing to accomplish the wash steps. The wash aspirator probe 74, also depended from second probe assembly 56, is connected through a solenoid activated valve 106 to a vacuum pump 108 through waste reservoirs 190a and 109b. These reservoirs are used to store fluids aspirated from the various reaction tubes. Each reservoir has a control valve 110 which determines where the liquid will be stored.

Substrate reagent, used in chromophore formation, is stored in substrate reservoir 111. Since precise amounts (e.g., 200 ml.) of substrate must be dispensed, a substrate syringe 112 is used to withdraw fluid from the reservoir 111. Solenoid-activated valves 114 and 116 open and close to permit or to restrict flow of substrate reagent to and from the reservoir 111 and to and from the substrate probe 66. A substrate motor 118 is used to aspirate substrate from the reservoir 111 into the syringe 112 and to deliver substrate reagent from the syringe 112 to the probe 66 which is depended from the second probe assembly 56.

Quench reagent, which is added to the substrate reagent after a suitable enzyme substrate incubation period, is stored in quench reservoir 120. Liquid level in reservoir 120 is maintained by a level sensor 121. Quench reagent is used in the chromophore detection sequence and is also used to wash the aspirator probe 49 free of contaminants. In the detection sequence, precise amounts of quench reagents are required to insure reproducible results, particularly as compared to standards. Less precise delivery of quench reagent is required for the aspirator probe 49 wash. To accommodate both of these operating modes, the quench delivery system includes a three way valve and pump 122. This valve 122 communicates alternatively with the quench probe 68, a quench syringe 124 and a probe wash 125. In FIG. 6, this valve-pump 122 is positioned to communicate with the syringe 124 and probe 68. Syringe 124 is driven by a quench syringe motor 126.

The final component of the reaction processor module seen in FIG. 6 is the optics section. This part of the module is intended to quantitatively measure the signal generated in the reaction tubes. While the specification makes reference to a chromophore, implying spectrophotometric detection, it will be appreciated by those skilled in the art that other species of detectable signal are possible without varying from the scope of the present invention. For example, it is contemplated that fluorometric determinations could be made in the optics section. Referring to FIG. 6, an optics aspirator probe 49 is depended from the first probe assembly 48. Quenched-substrate is withdrawn from the subject reaction tube through a flow cell 128 by the action of a peristaltic pump 130. The spectrophotometric or fluorometric measurements are made on the fluid as it flows through the optics flow cell 128. Fluid leaving the peristaltic pump 130 passes through solenoid activated valve 132 and is briefly stored in an enlarged section 133. After measurement in the optics flow cell 128, the direction of the peristaltic pump 130 is reserved and the fluid is made to flow back into the reaction tubes through the aspirator probe 49. The inside of the aspirator probe 49, the flow cell 128 and peristaltic pump 130 are washed with quench reagent when valve 134 is open and valve 132 is closed. This presents cross-contamination of sample results which leads to error in the technique.

Figure 7A:
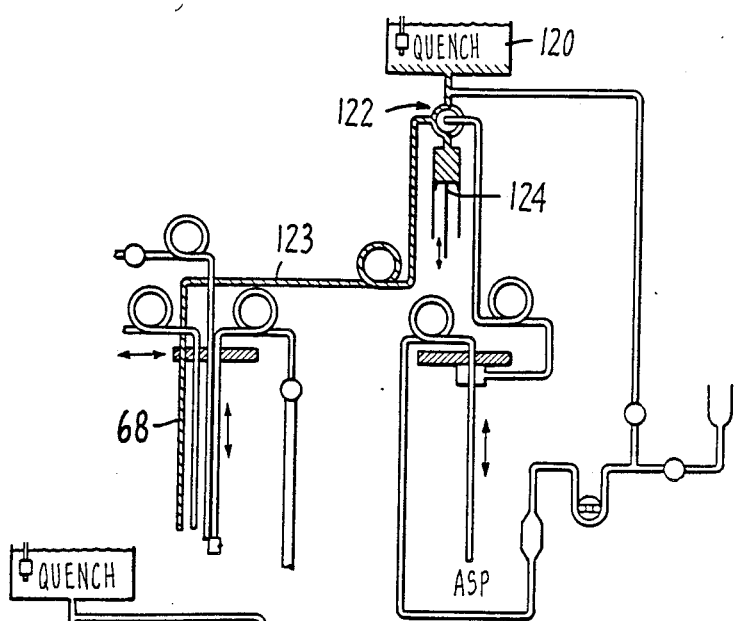
FIGS. 7A-7C are schematic flow diagrams illustrating operation of the present invention.
Figure 7B:
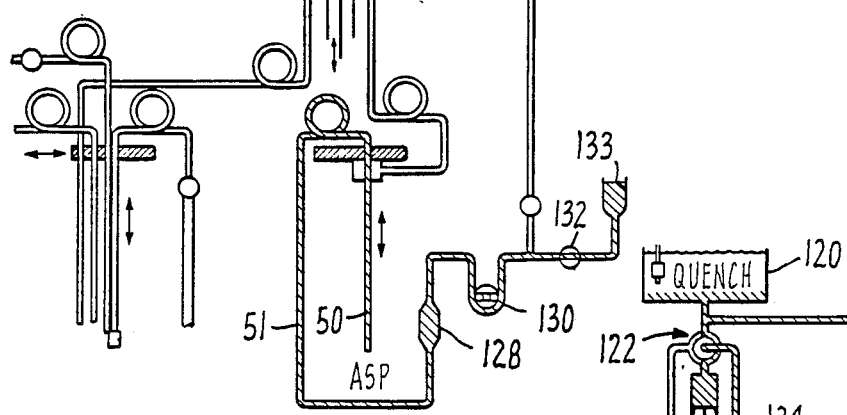
Figure 7C:
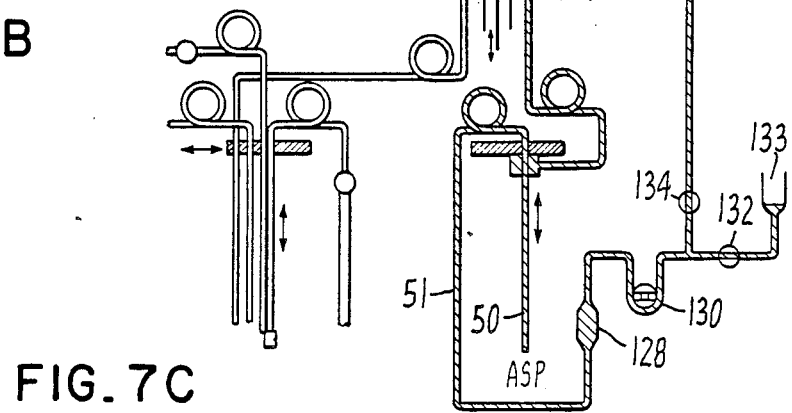

FIGS. 7A–7C illustrate the operation of the present invention. As shown in FIG. 7A diluent or quench reagent of a precise volume is drawn into the quench syringe 124 through quench valve 122 from quench reservoir 120. With the quench valve 122 changed in position the prescribed volume of quench reagent is directed through line 123 to the diluent/quench probe 68 and into one of the tubes on one row of the reagent tray.

As illustrated in FIG. 7B, simultaneously with the operation illustrated in FIG. 7A, a previously diluented/quenched sample in the correspondingly numbered tube in the succeeding row of tubes from the tube into which quench is being injected is aspirated by the optic probe 50 through line 51 and flow cell 128 by means of a peristaltic pump 130 and to a flow cell reservoir 133. The absorbance or fluorescence for the spectrophotometric or spectrofluorometric readings are made at the flow cell 128.

Next, as shown in FIG. 7C, the aspirate or optic probe 50 and the flow cell plumbing 51, 128 and 133 are back-flushed with quench reagent into the tube from which the sample has just been aspirated by optic probe 50 and read. Both the inside and the outside of the aspirate probe 50 are back-flushed. With the simultaneous diluent/quench reagent injected into one tube of one row and the sample solution in the corresponding by numbered tube of the succeeding row read and back-flushed into that tube, the carriage moves the probes of the first assembly onto the next tube in the row or, if the probes have operated on the last tube in the row, onto the first tube in the next row. When each of the tubes in the reagent tray has been first quenched and succeedingly read, the reaction tray is moved to the front of the instrument for removal.

The relationship between the optics module probe 50 and the diluent/quench probe 68 permits the solution to mix for a greater period of time than if the probes were immediately adjacent to each other. Further, the movement of the platform during these steps also creates a mixing force.

While the subject invention has been described with reference to a particular embodiment, it is understood that variations can be made which are within the intended scope of the invention and the claims appended hereto.

We claim:

1. In an apparatus for performing immunoassay techniques automatically on a rectangular rack of reaction tubes with the tubes arranged in rows separated by a given distance, an apparatus for adding a reagent and for transferring the resulting solution to an optics module which comprises:

a carriage;

a first probe assembly attached to the carriage;

a diluent/quench probe, which is subtended from the first probe assembly;

a second probe assembly attached to the carriage;

an optics module probe which is subtended from the second probe assembly;

a platform means for selectively positioning a rack of reaction tubes relative to the carriage with the tubes in the rack arranged in rows;

means for providing relative movement between the rack of reaction tubes and said first and second probe assemblies in a first direction parallel to a line through said diluent/quench probe and said optics probe and in a second direction substantially normal to said first direction;

said first and second probe assemblies arranged relative to each other such that the diluent/quench probe and the optics module probe are separated from each other by a distance equivalent to the given distance between rows of reaction tubes in the rectangular reaction tube rack along the line through said diluent/quench probe and said optics probe; and means for simultaneously operating said diluent/quench probe of said first probe assembly and said optics module probe of said second probe assembly on tubes in adjacent rows of the rack of tubes whereby the optics module probe can operate in performance of quantitative optical determination of sample in a tube in one row of the rack of tubes while the diluent/quench probe is simultaneously adding a reagent to a tube in the adjacent row of tubes and the reaction time for the reagent is no greater than the time to add reagent to the tubes in sequence between the tube in which the diluent/quench probe is operating and the tube in which the optics probe is operating.

2. The apparatus of claim 1 including means for lowering said diluent/quench probe and said optics module probe into respective sample tubes located therebelow and means for supporting said diluent/quench probe such that in lowered position said diluent/quench probe is above sample in the respective sample tube in which said diluent/quench probe is lowered.

3. In an apparatus for performing immunoassay techniques automatically on a rectangular rack of reaction tubes with the tubes arranged in rows separated by a given distance, an apparatus for adding a reagent and for transferring the resulting solution to an optics module which comprises:

a carriage;

a first probe assembly attached to the carriage;

a diluent/quench probe subtended from the first probe assembly;

a second probe assembly attached to the carriage;

an optics module probe subtended from the second probe assembly;

a platform means for selectively positioning a rack of reaction tubes relative to the carriage with the tubes in the rack arranged in rows;

means for providing relative movement between the rack of reaction tubes and said first and second probe assemblies in a first direction parallel to a line through said diluent/quench probe and said optics probe and in a second direction substantially normal to said first direction;

said first and second probe assemblies arranged relative to each other such that the diluent/quench probe and the optics module probe are separated from each other by a distance equivalent to the given distance between rows of reaction tubes in the rectangular reaction tube rack;

means for simultaneously lowering said diluent/quench probe and said optics module probe into respective tubes therebelow in adjacent rows of reaction tubes in said reaction tube rack;

means for injecting diluent/quench into one sample tube in one rack row; and means for aspirating diluted/quenched sample from another sample tube in the row succeeding said rack row substantially simultaneously with the injection of diluent/quench into said one sample tube whereby the optics module probe can operate in performance of quantitative optical determination of sample in a tube in one row of the rack of tubes while the diluent/quench probe is simultaneously adding a reagent to a tube in the adjacent row of tubes and the reaction time for the reagent is no greater than the time to add reagent to the tubes in sequence between said other sample tube and said one sample tube.

4. In the apparatus of claim 3 means for back-washing the aspirated diluted quenched sample with additional diluent/quench back into the other sample tube.

5. In the apparatus of claim 3 means supporting said diluent/quench probe from said first probe assembly such that in lowered position said diluent/quench probe is above sample in said one sample tube in which said diluent/quench probe is located.

* * * * *